(12) United States Patent
Kato et al.

(10) Patent No.: US 9,717,410 B2
(45) Date of Patent: Aug. 1, 2017

(54) OPHTHALMOLOGIC APPARATUS

(71) Applicant: Tomey Corporation, Nagoya-shi (JP)

(72) Inventors: Chihiro Kato, Nagoya (JP);
Katsumasa Okouchi, Nagoya (JP)

(73) Assignee: Tomey Corporation, Nagoya-shi (JP)

(*) Notice: Subject to any disclaimer, the term of this patent is extended or adjusted under 35 U.S.C. 154(b) by 233 days.

(21) Appl. No.: 14/627,260

(22) Filed: Feb. 20, 2015

(65) Prior Publication Data

US 2015/0230705 A1 Aug. 20, 2015

(30) Foreign Application Priority Data

Feb. 20, 2014 (JP) ................................ 2014-030201

(51) Int. Cl.
*A61B 3/10* (2006.01)
*A61B 3/117* (2006.01)
*A61B 3/14* (2006.01)
*A61B 3/00* (2006.01)

(52) U.S. Cl.
CPC ............ *A61B 3/117* (2013.01); *A61B 3/0008* (2013.01); *A61B 3/0058* (2013.01); *A61B 3/1025* (2013.01); *A61B 3/14* (2013.01)

(58) Field of Classification Search
CPC ... A61B 3/0025; A61B 3/0058; A61B 3/1005; A61B 3/1015; A61B 3/102; A61B 3/1025; A61B 3/117; A61B 3/1173
USPC ................. 351/205, 206, 212, 246
See application file for complete search history.

(56) References Cited

U.S. PATENT DOCUMENTS

| 8,690,328 | B1 | 4/2014 | Chong | |
|---|---|---|---|---|
| 2007/0002277 | A1 | 1/2007 | Hanebuchi | |
| 2007/0279592 | A1 | 12/2007 | Hanebuchi | |
| 2012/0200827 | A1* | 8/2012 | Kato ................ | A61B 3/1005 351/221 |
| 2013/0242259 | A1 | 9/2013 | Hacker et al. | |

FOREIGN PATENT DOCUMENTS

| EP | 2484273 A1 | 8/2012 |
|---|---|---|
| JP | 2007-37984 A | 2/2007 |
| JP | 2007-313208 A | 12/2007 |
| JP | 2014-144178 A | 8/2014 |

OTHER PUBLICATIONS

European Search Report for EP15155638 mailed on Jun. 26, 2015 (5 pages).

* cited by examiner

*Primary Examiner* — Huy K Mai
(74) *Attorney, Agent, or Firm* — Shumaker, Loop & Kendrick, LLP

(57) ABSTRACT

An ophthalmologic apparatus measures a dimension of an eye to be examined. The ophthalmologic apparatus includes a light source, an incidence member, an acquisition unit, and a display unit. The incidence member causes light from the light source to be incident on a plurality of different positions in the eye to be examined. The acquisition unit acquires a two-dimensional tomographic image of an interior of the eye to be examined on the basis of a plurality of interference signals acquired as a result of the incidence member causing the incidence of light on the plurality of different positions. The display unit displays the acquired two-dimensional tomographic image.

8 Claims, 14 Drawing Sheets a: Average of Axial Length of Eye
b: Standard Deviation
c: Axial Length of Eye
d: Anterior Chamber Depth
e: Lens
f: Corneal Thickness a: Average of Axial Length of Eye
b: Standard Deviation a: Average of Axial Length of Eye
b: Standard Deviation
c: Axial Length of Eye
d: Anterior Chamber Depth
e: Lens
f: Corneal Thickness a: Average of Axial Length of Eye
b: Standard Deviation
c: Axial Length of Eye
d: Anterior Chamber Depth
e: Lens
f: Corneal Thickness a: Average of Axial Length of Eye
b: Standard Deviation a: Average of Axial Length of Eye
b: Standard Deviation
c: Axial Length of Eye
d: Anterior Chamber Depth
e: Lens
f: Corneal Thickness a: Average of Axial Length of Eye
b: Standard Deviation
c: Axial Length of Eye
d: Anterior Chamber Depth
e: Lens
f: Corneal Thickness

OPHTHALMOLOGIC APPARATUS

CROSS-REFERENCE TO RELATED APPLICATION

This application claims priority to Japanese Patent Application No. 2014-030201 filed on Feb. 20, 2014, the contents of which are hereby incorporated by reference into the present application.

TECHNICAL FIELD

The present teachings relate to an ophthalmologic apparatus for eye examination, and more particularly to an ophthalmologic apparatus that determines a position of a measuring portion (for example, crystalline lens and retina) inside an eye.

DESCRIPTION OF RELATED ART

An ophthalmologic apparatus for examining an interior (for example, crystalline lens and retina) of an eye is being developed. The ophthalmologic apparatus of this type is provided with an optical measurement system that radiates light from a light source to inside the eye to be examined and guides the reflected light therefrom, and an optical reference system that radiates light from the light source to a reference surface and guides the reflected light therefrom. A position of a measuring portion (for example, the crystalline lens and retina) inside the eye to be examined is determined from the interfering light between the reflected light guided by the optical measurement system and the reflected light guided by the optical reference system. Conventional examples of ophthalmologic apparatuses of this type are disclosed in Japanese Patent Application Publication Nos. 2007-37984 and 2007-313208.

BRIEF SUMMARY OF INVENTION

In the conventional ophthalmologic apparatuses such as disclosed in Japanese Patent Application Publication Nos. 2007-37984 and 2007-313208, when the eye to be examined is examined, the optical axis of the light radiated to the eye is adjusted to match the axis of vision of the eye, a position of a measuring portion inside the eye is determined from the interference signal obtained from one optical axis, values such as an anterior chamber depth (ACD) and an axial length of the eye are calculated from the determined position, and those values are displayed on a monitor or the like. One-dimensional information (also referred to as "A-scan image") representing the intensity of the interference signal with respect to the depth distance of the eye, such as shown in FIG. 4 or FIG. 5 of Japanese Patent Application Publication No. 2007-313208, is also displayed. An examiner checks the A-scan image and estimates the obtained value such as the axial length of the eye.

However, since the A-scan image and the value such as the axial length of the eye, which are displayed on the monitor, are obtained from one optical axis, where a retina signal is weak, for example, due to opacity in the crystalline lens, or where there is a disease in the retina, the obtained value of the axial length of the eye or the like is difficult to estimate in the conventional A-scan image obtained from one optical axis, and the correct value sometimes cannot be obtained.

Furthermore, sometimes the value such as the axial length of the eye cannot be obtained due to the crystalline lens opacity or retina disease, or only values of low reliability and a large spread among the measurements are obtained.

With the foregoing in view, it is an object of the present teachings to provide an ophthalmologic apparatus in which a plurality of interference signals are obtained at a plurality of optical axes at different positions in an eye to be examined, wherein a more accurate value such as an axial length of the eye can be acquired by acquiring a two-dimensional tomographic image of an interior of the eye on the basis of the obtained plurality of interference signals and determining a position of a measuring portion inside the eye from the acquired two-dimensional tomographic image.

The ophthalmologic apparatus disclosed in the present description is provided with an optical measurement system that uses light interference to measure dimensions of the eye to be examined, and further includes an incidence member that causes light from a light source to be incident on a plurality of different positions in the eye to be examined, and a display unit for acquiring a two-dimensional tomographic image of an interior of the eye to be examined on the basis of a plurality of interference signals acquired using the incidence member and displaying the acquired two-dimensional tomographic image.

In the ophthalmologic measuring apparatus, since the two-dimensional tomographic image of the interior of the eye which is based on the interference signals obtained from a plurality of optical axes at different positions of the eye to be examined is displayed on the monitor, the state of crystalline lens opacity or the state of retina can be visually checked and the obtained value such as the axial length of the eye can be estimated more accurately.

DETAILED DESCRIPTION OF INVENTION

Figure 1:
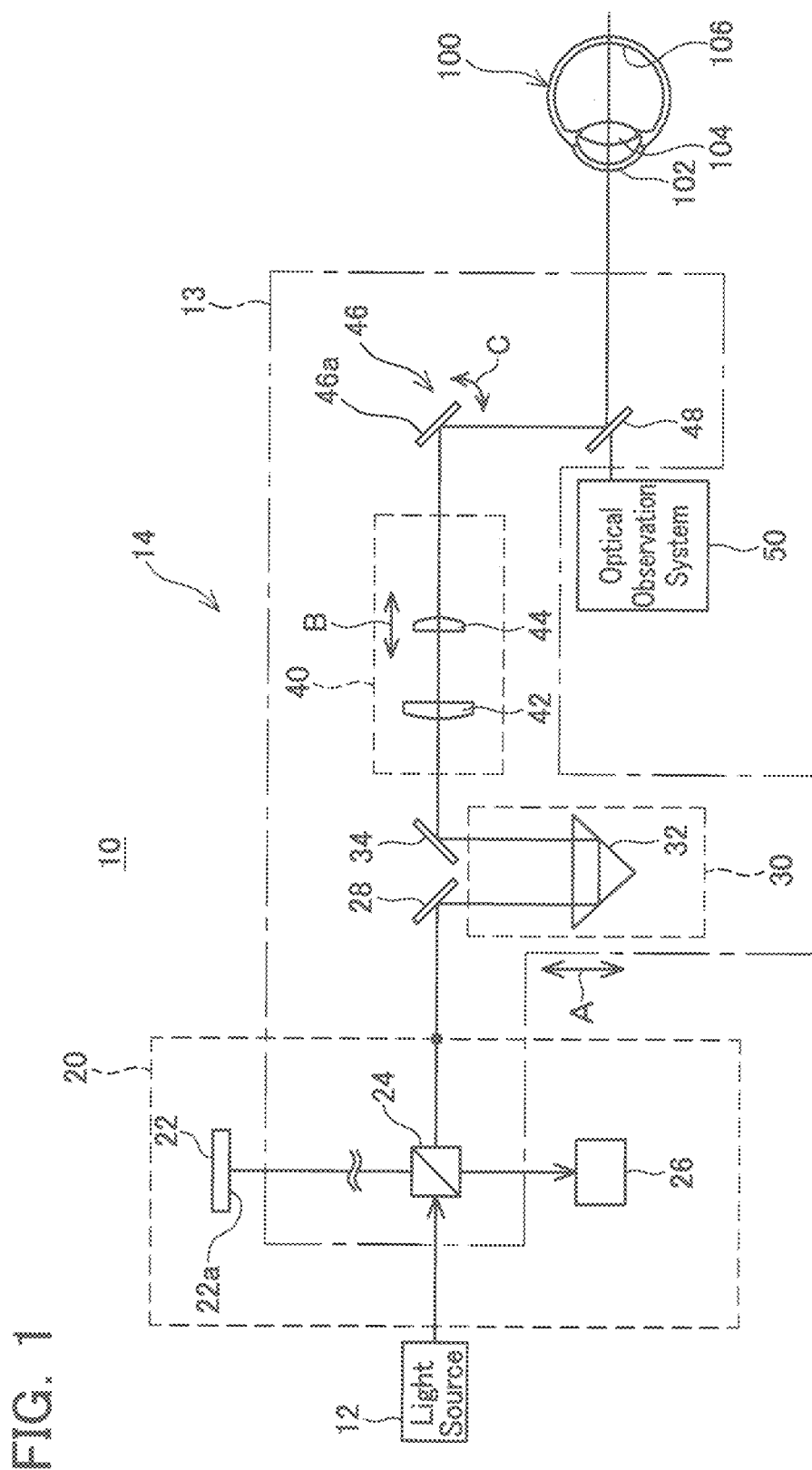
FIG. 1 is a schematic configuration diagram of an optical system of an ophthalmologic apparatus according to the present embodiment.

The ophthalmologic apparatus disclosed in the present description has a calculation unit that calculates an ophthalmologic measurement value of the eye to be examined on the basis of the acquired two-dimensional tomographic image. Image processing such as averaging processing or smoothing processing is implemented to determine the position of the measuring portion (cornea, crystalline lens, retina, and the like) inside an eye on the basis of the two-dimensional tomographic image, a measurement error caused by the lens opacity, state of retina, or the like is reduced, the determination accuracy of the position of the measuring portion is increased, and a value such as the axial length of the eye can be calculated with good accuracy.

Further, the ophthalmologic apparatus disclosed in the present description has a correction unit that corrects the ophthalmologic measurement value from the two-dimensional tomographic image of the eye interior displayed by a display unit. Each position of the measuring portion inside the eye which has been determined by the apparatus can be corrected while checking the two-dimensional tomographic image, and a more accurate value can be obtained.

The correction unit in the ophthalmologic apparatus disclosed in the present description includes a first designation unit for randomly designating one or more positions with respect to the two-dimensional tomographic image of the interior of the eye to be examined which is displayed by the display unit, the measurement value being corrected on the basis of the designated position. As a result, each position of the measurement object in the interior of the eye to be examined can be easily and accurately corrected.

Further, in the ophthalmologic apparatus disclosed in the present description, the plurality of interference signals acquired by the incidence member is subjected to averaging processing, and a one-dimensional information (A-scan image) in the depth direction of the eye to be examined is displayed. The measurement value can thus be estimated more accurately by also displaying the A-scan image which has been displayed in the conventional ophthalmologic apparatuses. Furthermore, since the A-scan image which is to be displayed is obtained by averaging the plurality of interference signals, the A-scan image which is more accurate than the A-scan image which has been displayed in the conventional ophthalmologic apparatuses can be displayed.

Further, the ophthalmologic apparatus disclosed in the present description has a second designation unit that designates one or more positions in a direction perpendicular (up-down direction on a screen) to a depth direction (Z direction) of the eye to be examined with respect to the two-dimensional tomographic image of the interior of the eye to be examined which has been displayed by the display unit, and one or more one-dimensional information (A-scan images) in the depth direction of the eye to be examined at one or more designated positions (optical axes) are displayed. As a result, the one-dimensional information (A-scan images) at positions (optical axes) designated in the two-dimensional tomographic image are displayed, as appropriate. Therefore, wavelengths or intensities of the interference signals can be visually determined, the presence or position of noise can be checked in detail, and more accurate correction can be performed.

Further, in the ophthalmologic apparatus disclosed in the present description, the one-dimensional information (A-scan image) and the two-dimensional tomographic image of the interior of the eye to be examined are displayed in parallel. Since the A-scan image can be checked in detail while observing the two-dimensional tomographic image, more accurate ophthalmologic measurements are facilitated and reliability of the obtained measurement values can be increased.

Embodiment

As shown in FIG. 1, an ophthalmologic apparatus of the present embodiment comprises a measurement unit 10 for examining an eye 100 to be examined. The measurement unit 10 comprises an optical interference system 14 that causes interference of a reflected light that is reflected from the eye 100 and a reference light, an optical observation system 50 that observes an anterior part of the eye 100, and an optical alignment system (not shown in the figure) for aligning the measurement unit 10 with respect to the eye 100 in a predetermined positional relationship. An optical alignment system that has been used in a well-known ophthalmologic apparatus can be used as the aforementioned optical alignment system, and detailed explanation thereof is herein omitted.

The optical interfering system 14 is configured by a light source 12, an optical measurement system 13 that radiates light from the light source 12 to inside the eye 100 and guides reflected light thereof, an optical reference system (22, 24) that radiates light from the light source 12 to a reference surface 22a and guides the reflected light thereof, and a photo detector 26 that detects interfering light between the reflected light guided by the optical measurement system 13 and the reflected light guided by the optical reference system (22, 24).

The light source 12 is of a wavelength sweep type, and a wavelength of the emitted light changes with a predetermined period. Where the wavelength of the light emitted from the light source 12 changes, the reflection position of the reflected light that causes interference with the reference light changes correspondingly to the wavelength of the emitted light. This change in the reflection position takes place in the depth direction of the eye 100. Therefore, the position of each portion (that is, a crystalline lens 104, a retina 106 and the like) inside the eye 100 can be determined by measuring the interfering light, while changing the wavelength of the emitted light.

The optical measurement system 13 is constituted by a beam splitter 24, a mirror 28, a 0 point adjustment mechanism 30, a mirror 34, a focal point adjustment mechanism 40, an incident angle adjustment mechanism 46, and a hot mirror 48. The light emitted from the light source 12 irradiates the eye 100 via the beam splitter 24, mirror 28, 0 point adjustment mechanism 30, mirror 34, focal point adjustment mechanism 40, incident angle adjustment mechanism 46, and hot mirror 48. The reflected light from the eye 100 is guided to the photo detector 26 via the hot mirror 48, incident angle adjustment mechanism 46, focal point adjustment mechanism 40, mirror 34, 0 point adjustment mechanism 30, mirror 28, and beam splitter 24. The 0 point adjustment mechanism 30, focal point adjustment mechanism 40, and incident angle adjustment mechanism 46 will be described in detail hereinbelow.

The optical reference system is constituted by the beam splitter 24 and a reference mirror 22. Part of the light emitted from the light source 12 is reflected by the beam splitter 24, radiated to the reference mirror 22, and reflected by the reference mirror 22. The light reflected by the reference mirror 22 is guided to the photo detector 26 via the beam splitter 24. The reference mirror 22, beam splitter 24, and photo detector 26 are disposed inside an interferometer 20, and the positions thereof are fixed. Therefore, in the ophthalmologic apparatus of the present embodiment, the reference optical path length of the optical reference system is constant and does not change.

The photo detector 26 detects the interfering light between the light guided by the optical reference system and the light guided by the optical measurement system. For example, a photodiode can be used as the photo detector 26.

The optical observation system 50 radiates observation light via the hot mirror 48 on the eye 100 and picks up the reflected light that is reflected from the eye 100 (that is, the reflected light of the radiated observation light). In this case, the hot mirror 48 reflects light from the light source 12 of the optical interference system and transmits light from the light source of the optical observation system 50. As a result, in the ophthalmologic apparatus of the present embodiment, it is possible to perform measurements with the optical interference system and observations of the anterior eye part with the optical observation system 50 at the same time. An optical observation system that has been used in a well-known ophthalmologic apparatus can be used as the optical observation system 50. For this reason, detailed configuration thereof is not explained herein.

Figure 2:
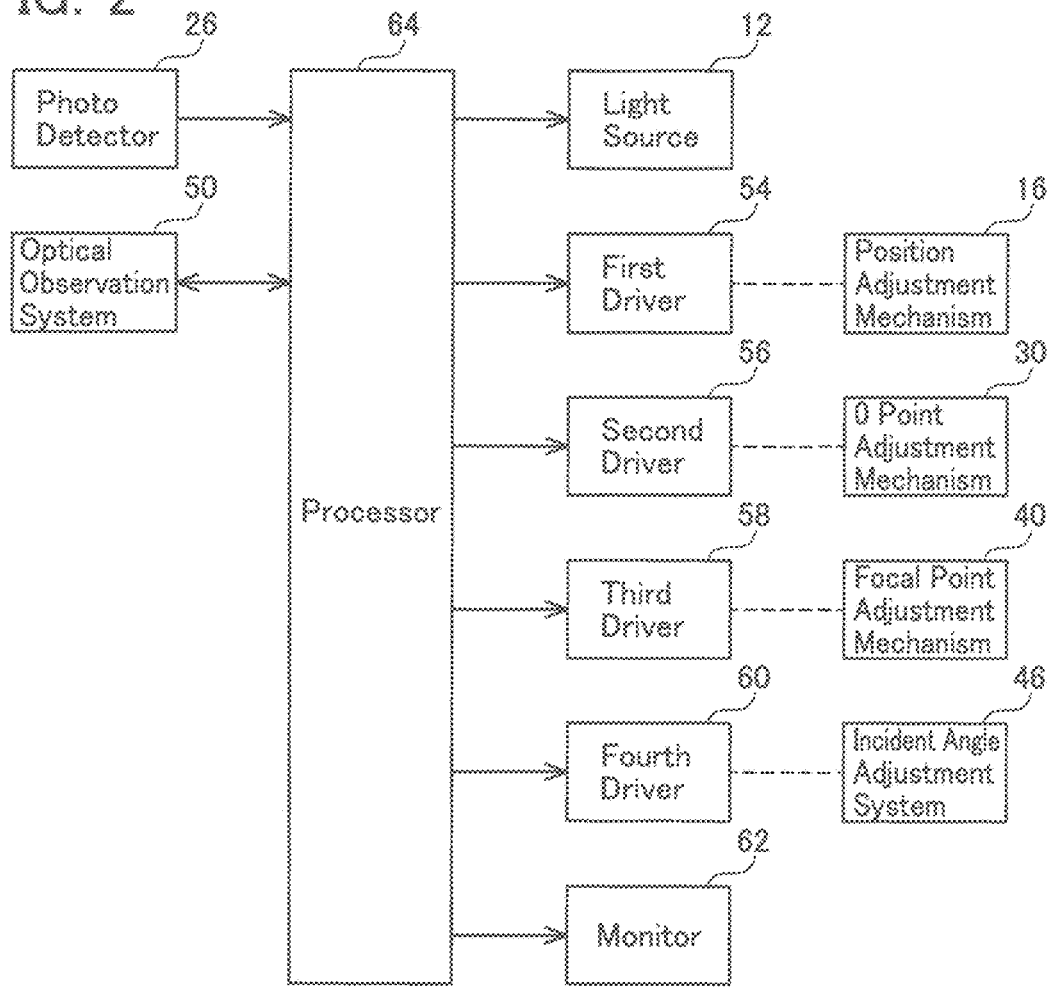
FIG. 2 is a block-diagram of a control system of the ophthalmologic apparatus according to the present embodiment.
Figure 3:
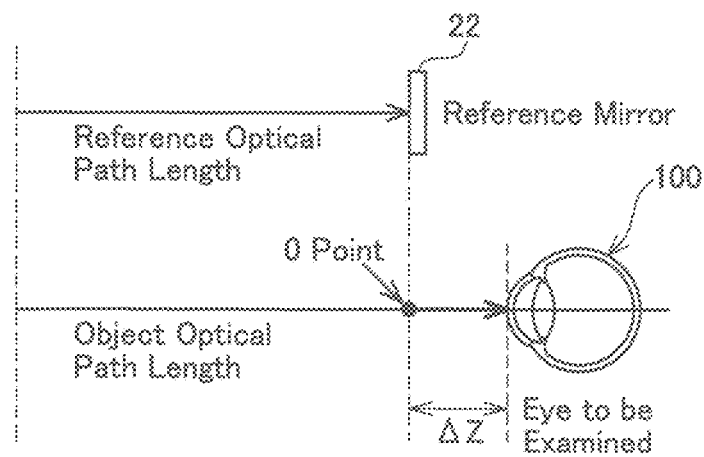
FIG. 3 illustrates functions of a 0 point adjustment mechanism.

The 0 point adjustment mechanism 30, focal point adjustment mechanism 40, and incident angle adjustment mechanism 46 used in the optical measurement system will be explained below. The 0 point adjustment mechanism 30 is provided with a corner cube 32, and a second driver 56 (shown in FIG. 2) that moves the corner cube 32 back and forth with respect to the mirrors 28 and 34. Where the second driver 56 moves the corner cube 32 in the direction of arrow A in FIG. 1, the optical path length (that is, the object optical path length of the optical measurement system) from the light source 12 to the eye 100 changes. As shown in FIG. 3, when there is an optical path difference Δz between the object optical path length from the light source 12 to the detection surface of the eye 100, which is the cornea surface in FIG. 3 (more specifically, light source 12 to detection surface plus detection surface to photo detector 26) and the reference optical path length from the light source 12 to the reference mirror 22 (more specifically, light source 12 to reference mirror 22 plus reference mirror 22 to photo detector 26) is present, the larger the optical path difference Δz, the lower is the intensity of interfering light between the reflected light that is reflected from the detection surface and the reference light. Conversely, the smaller the optical path difference Δz, the higher is the intensity of interfering light. Therefore, in the present embodiment, by changing the object optical path length with the 0 point adjustment mechanism 30, it is possible to change the position in which the reference optical path length and the object optical path length match (that is, the 0 point) from the surface of the cornea 102 to the surface of the retina 106.

Figure 4D:
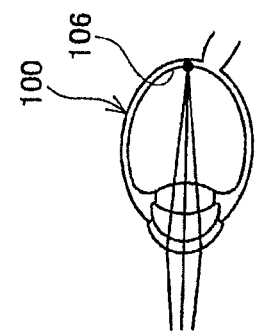
FIGS. 4A to 4D illustrate functions of a focal point adjustment mechanism.
Figure 4C:
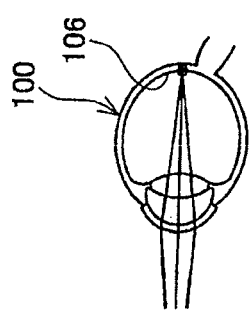
Figure 4B:
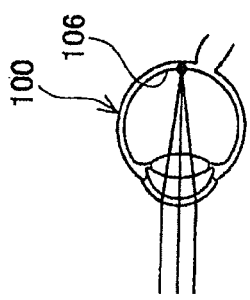
Figure 4A:
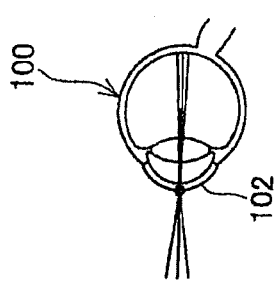

The focal point adjustment mechanism 40 is provided with a convex lens 42 disposed on the light source 12 side, a convex lens 44 disposed on the eye 100 side, and a third driver 58 (shown in FIG. 2) that moves the convex lens 44 back and forth with respect to the convex lens 42 in the focal aim direction. The convex lens 42 and the convex lens 44 are disposed on the focal aim and change a position of a focal point of incident parallel light from the light source 12. Thus, where the third driver 58 drives the convex lens 44 in the direction of arrow B in FIG. 1, the position of the focal point of the light radiated to the eye 100 changes in the depth direction of the eye 100. More specifically, where the convex lens 44 is moved toward the eye 100 from the state in which the distance between the convex lens 42 and the convex lens 44 adjusted so that the light radiated from the convex lens 44 becomes parallel light, the light radiated from the convex lens 44 becomes converged light; and where the convex lens 44 is moved toward the convex lens 42, the light emitted from the convex lens 44 becomes diverging light. Therefore, by adjusting the distance between the convex lens 42 and the convex lens 44, it is possible to change the position of the focal point of the radiated light with respect to the eye 100 of normal vision from the surface of the cornea 102 to the surface of the retina 106, as shown in FIGS. 4A and 4B. Further, the position of the focal point of the radiated light can be also adjusted so as to become the position of the retina 106 with respect to the myopic eye shown in FIGS. 4C and 4D. Thus, by matching the position of the focal point of the light radiated to the eye 100 with the surface of the cornea 102 or the surface of the retina 106 of the eye 100, it is possible to increase the intensity of light reflected from these surfaces and detect the position of these surface with good accuracy.

Figure 5:
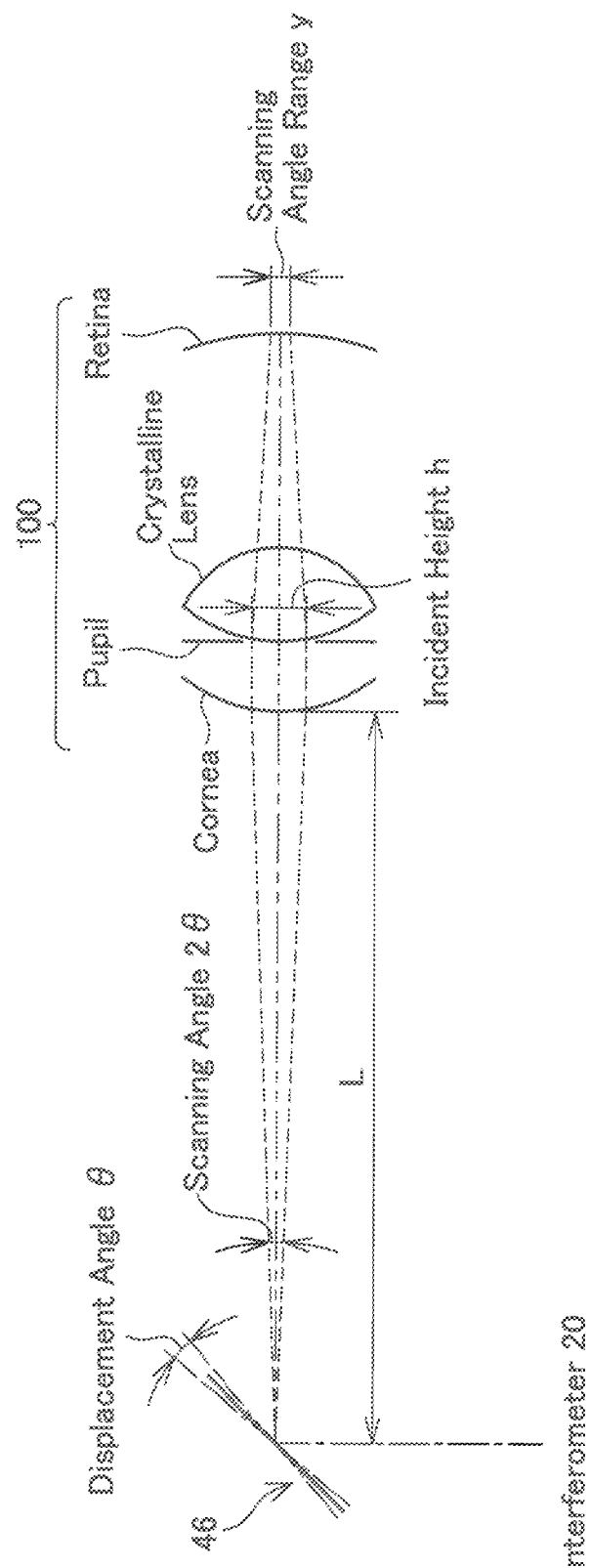
FIG. 5 illustrates functions of a galvano mirror.

The incident angle adjustment mechanism 46 is provided with a galvano mirror 46a and a fourth driver 60 that drives the galvano mirror 46a. The galvano mirror 46a is disposed on the focal aim and can be tilted within a predetermined angular range (for example, ±1°) with respect to the focal aim. Where the fourth driver 60 moves the galvano mirror 46a within the predetermined angular range, the incident position and incident angle of the light radiated to the eye 100 change. Thus, as shown in FIG. 5, the incident position and incident angle of the light on the cornea 102 change according to the displacement angle θ of the galvano mirror 46a. As a result, the incident position and incident angle of the light on the crystalline lens 104 change and the incident position of the light on the retina also changes. Therefore, even if the normal direction of the crystalline lens 104 shifts from the axis of vision, the light can be radiated substantially perpendicularly to the crystalline lens 104. As a result, the intensity of light reflected from the crystalline lens 104 is increased and the position of the crystalline lens 104 can be detected accurately. Further, even when a lens opacity is present in the crystalline lens 104 due to cataract or the like, light irradiation can be performed by avoiding the lens opacity. As a result, the intensity of light transmitted by the crystalline lens 104 can be increased and the position of the retina 106 can be accurately detected.

In the ophthalmologic apparatus of the present embodiment, the tilting direction of the galvano mirror 46a is set so that the incident position of the light radiated to the eye 100 changes in the transverse direction (i.e., direction connecting the left and right eyes). Therefore, the occurrence of the event in which the eye 100 is not irradiated with the light from the light source 12 because of eyelids or eyelashes is prevented.

The ophthalmologic apparatus of the present embodiment is also provided with a position adjustment mechanism 16 (shown in FIG. 2) for adjusting the position of the measurement unit 10 (more specifically, the optical system of the portion of the measurement unit 10 other than the interferometer 20) with respect to the eye 100 and a first driver 54 (shown in FIG. 2) that drives the position adjustment mechanism 16. As clearly follows from FIG. 5, where the position of the measurement unit 10 with respect to the eye 100 is adjusted and the distance L from the eye 100 to the galvano mirror 46a changes, the incident position of the light radiated to the eye 100 also changes accordingly. Therefore, by adjusting the distance L from the eye 100 to the galvano mirror 46a, it is possible to cause the incidence of light on the desired range of the crystalline lens 104. As a result, the lens opacity of the crystalline lens 104 can be adequately avoided. It is also preferred that the distance L from the eye 100 to the galvano mirror 46a be adjusted so that the light radiated to the eye 100 change within the range of the pupil.

The configuration of the control system of the ophthalmologic apparatus of the present embodiment will be described below. As shown in FIG. 2, the ophthalmologic apparatus is controlled by a processor 64. The processor 64 may be constituted by a microcomputer (microprocessor) constituted by CPU, ROM, RAM, and the like. The light source 12, the first to fourth drivers 54 to 60, a monitor 62, and the optical observation system 50 are connected to the processor 64. The processor 64 performs ON/OFF control of the light source 12 and controls the first to fourth drivers 54 to 60, thereby driving the mechanisms 16, 30, 40, and 46. The processor also controls the optical observation system 50 and displays the anterior eye part image picked up by the optical observation system 50 on the monitor 62. The photo detector 26 is also connected to the processor 64, and the interference signal corresponding to the intensity of the interfering light detected by the photo detector 26 is inputted to the processor 64. The processor 64 performs Fourier transform of the interference signal from the photo detector 26 to determine positions of various portions of the eye 100 (e.g., the front and rear surfaces of the cornea 102, front and rear surfaces of the crystalline lens 104, and the surface of the retina 106) and calculate the axial length of the eye 100. The processing performed by the processor 64 to determine the positions of portions of the eye 100 to be examined will be described below in greater detail.

Figure 8:
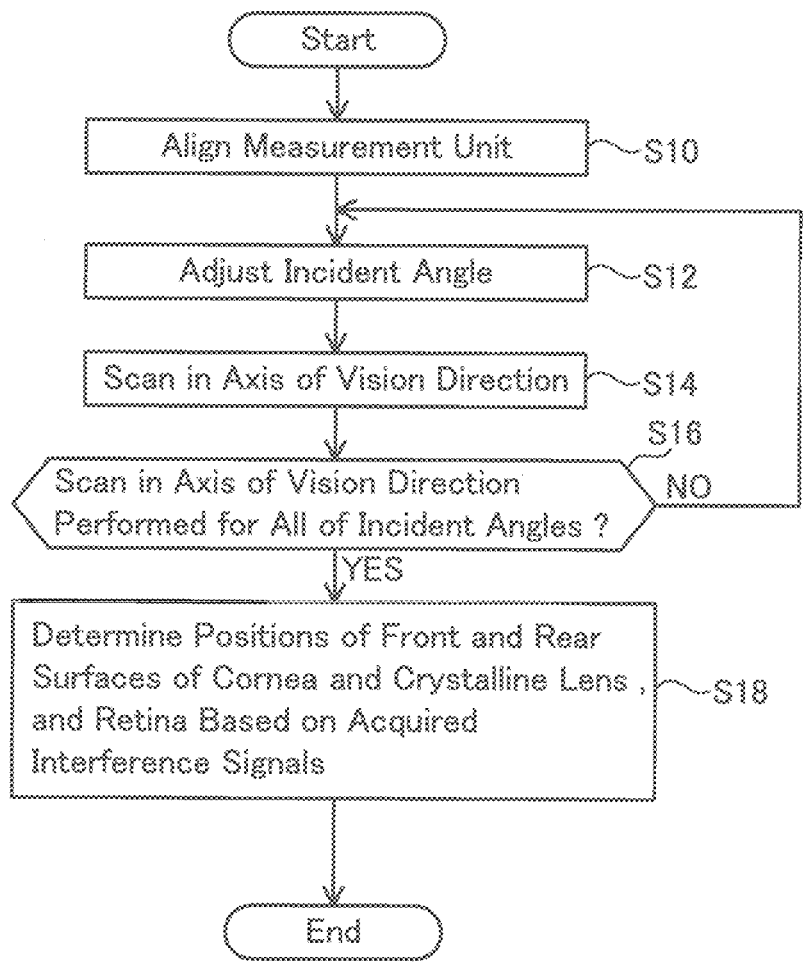
FIG. 8 is a flowchart illustrating an example of processing procedure performed in the ophthalmologic apparatus according to the present embodiment.

The procedure used to measure the axial length of the eye to be examined by using the ophthalmologic apparatus of the present embodiment will be explained below. As shown in FIG. 8, the operator aligns the measurement unit 10 with respect to the eye 100 by operating an operation member such as a joystick (not shown) (S10). Thus, in response to the operation of the operation member performed by the operator, the processor 64 drives the position adjustment mechanism 16 with the first driver 54. As a result, the position in the xy directions (i.e., longitudinal and lateral directions) and the position in the z direction (i.e., back-forth direction) of the measurement unit 10 with respect to the eye 100 are adjusted. The processor 64 also drives the second and third drivers 56 and 58 to adjust the 0 point adjustment mechanism 30 and the focal point adjustment mechanism 40. As a result, the position of the focal point of the light radiated from the light source 12 to the eye 100 assumes a predetermined position in the eye 100 (for example, the front surface of the cornea 102), and the position of 0 point where the object optical path length and reference optical path length match assumes a predetermined position in the eye 100 (for example, the front surface of the cornea 102).

Figure 6:
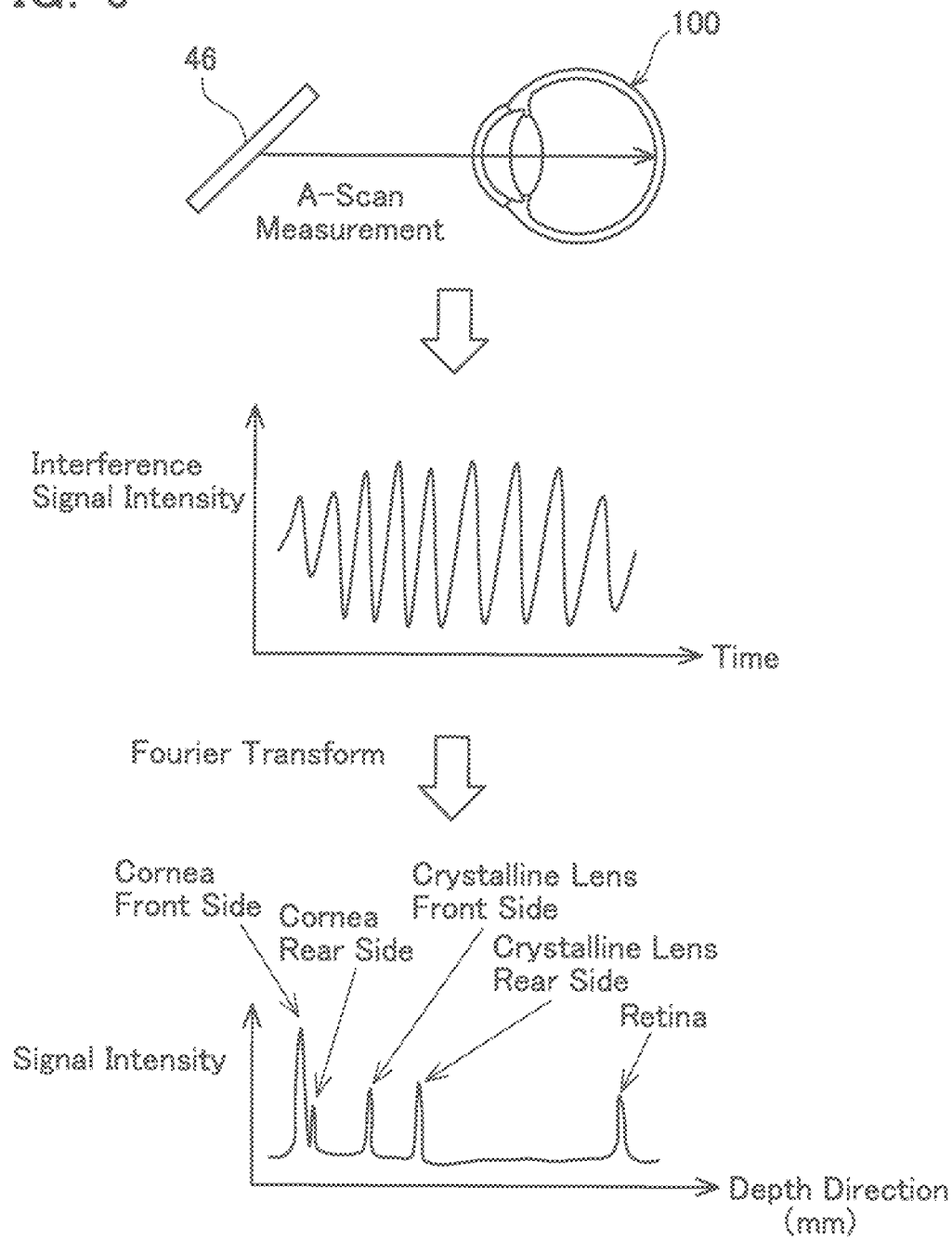
FIG. 6 illustrates the procedure of processing an interference signal waveform obtained when an optical path length of an optical measurement system is scanned within a predetermined optical path length range.

The processor 64 then drives the fourth driver 60 and adjusts the galvano mirror 46a to a scan angle within a scan angle range (S12). As a result, the light from the light source 12 falls on the eye 100 at the incident position and incident angle corresponding to the adjusted scan angle.

Where the adjustment of the galvano mirror 46a is completed, the processor 64 takes in the signal detected by the photo detector 26, while changing the frequency of light radiated from the light source 12 (S14). As has already been explained, where the frequency of light radiated from the light source 12 changes, the position where the measurement light interferes with the reference light and an interfering wave is generated changes in the depth direction of the eye 100. Therefore, the interference signal outputted from the photo detector 26 becomes a signal with intensity changing with time, as shown in FIG. 6, and this signal includes signals created by the interfering wave between the reference light and reflected light that has been reflected from various parts (e.g., front surface and rear surface of the cornea 102, front surface and rear surface of the crystalline lens 104, and surface of the retina 106) of the eye 100. Accordingly, the processor 64 performs Fourier transform of the signal inputted from the photo detector 26, thereby separating the interference signal component created by the reflected light reflected from various parts (e.g., front surface and rear surface of the cornea 102, front surface and rear surface of the crystalline lens 104, and surface of the retina 106) of the eye 100. The processor 64 thus can determine the positions of various portions of the eye 100 to be examined. In the present description, the process of changing the position where the interference occurs in the depth direction of the eye 100 by changing the frequency of the light radiated from the light source 12 is called A-scan.

Figure 7:
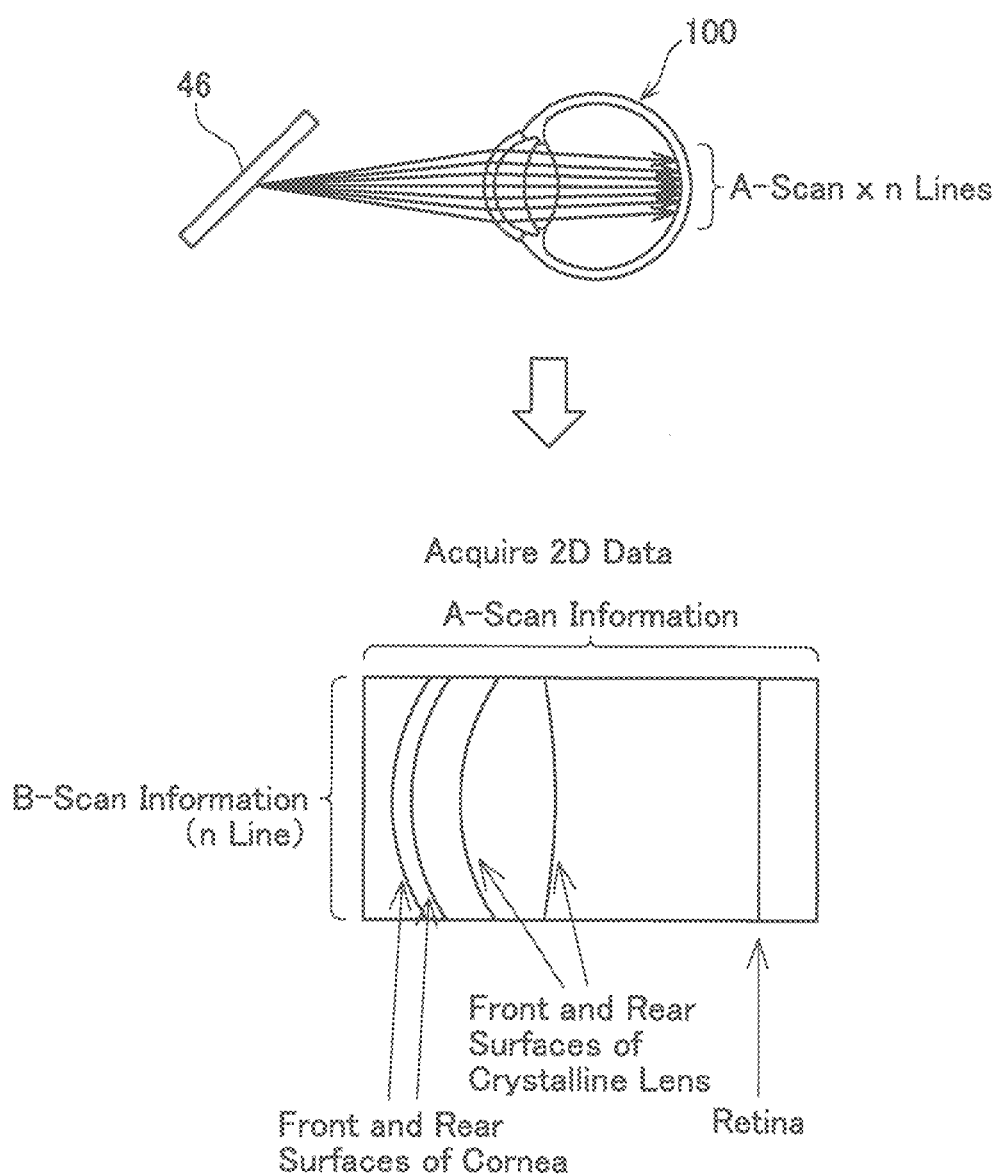
FIG. 7 illustrates a procedure of scanning an incident angle of light on an eye to be examined within the predetermined angular range and determining positions of each portion of the eye from information (i.e., information obtained by the procedure shown in FIG. 6) obtained with respect to each scan angle.
Figure 9:
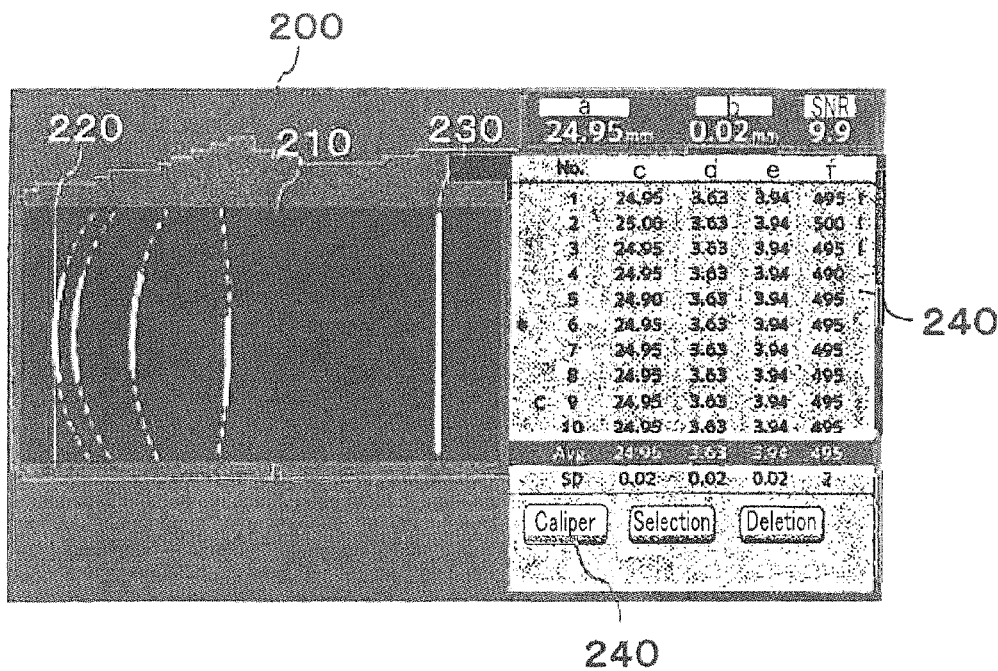
FIG. 9 is an example of a screen display displayed on a monitor (two-dimensional tomographic image display).

The processor 64 then determines whether or not the measurement of the above-described step S14 has been performed with respect to all of the scan angles (that is, all of the incident positions and incident angles) (S16). Where the measurement of step S14 has not been performed with respect to all of the scan angles (NO in step S16), the processing is returned to step S12 and repeated from step S12. As a result, the interference signal obtained by A-scan is acquired for each scan angle of the galvano mirror 46a. In the present description, the process of changing the incident position and incident angle of light from the light source 12 by changing the scan angle (oscillation angle θ) of the galvano mirror 46a is called B-scan.

Where the measurement of step S14 has been performed with respect to all of the scan angles (YES in step S16), the processor 64 determines the position of each portion of the eye 100 (that is, the positions of the front surface and rear surface of the cornea 102, front surface and rear surface of the crystalline lens 104, and surface of the retina 106) (S18). More specifically, where the processing of step S14 is performed with respect to each scan angle, information on interference signals (i.e., A-scan information) is acquired with respect to each scan angle. Therefore, as shown in FIG. 7, two-dimensional information is obtained in which interference signal information (i.e., A-scan information) is arranged in a row correspondingly to the number (n) of scan angles. Therefore, by calculating the average value of position information of the portions of the eye 100 that is included in each type of interference signal information (that is, the front surface and rear surface of the cornea 102, front surface and rear surface of the crystalline lens 104, and surface of the retina 106), the processor 64 determines the position of each portion of the eye 100. Where the position of each portion of the eye 100 can be determined, the processor 64 calculates the axial length of the eye 100. The position of each portion of the eye 100 and the axial length of the eye calculated in the above-described manner are displayed on the monitor 62.

Where the position of each portion of the eye 100 can be determined, the processor 64 calculates the axial length of the eye 100. The position of each portion and the axial length of the eye 100 which have thus been calculated or the two-dimensional tomographic image in the depth direction of the eye which has been acquired form the two-dimensional information is displayed on the monitor 62, for example, as depicted in FIG. 9. FIG. 9 shows an example of a screen display in which the position of each portion and the value of the axial length of the eye 100 calculated on the monitor screen 200 are displayed in the data display portion 240, and the two-dimensional tomographic image in the depth direction of the eye is displayed in the image display portion 210. The lines 220 and 230 in the image display portion 210 are the calculated position (220) of the front surface of the cornea and retina position (230) of the eye 100. Ten measurement values and the average value thereof are displayed in the data display portion 240, but such data display is not limiting and only one measurement value may be displayed, or more than ten measurement values may be displayed. Further, it is not always necessary to display the average value (Avg.) or standard deviation (SD). Where the two-dimensional tomographic image in the depth direction of the eye is thus displayed in the image display portion 210, the examiner can estimate the measurement result of the data display portion 240 while checking the two-dimensional tomographic image in the image display portion 210.

Where the examiner determines that the position (220) of the front surface of the cornea and the retina position (230) of the eye 100 which are displayed in the two-dimensional tomographic image in the image display portion 210 are not adequate, the examiner can repeat the measurements or designate and correct the position of the front surface of the cornea and the retina position of the eye 100 by manually pressing the caliper button 240.

Figure 10:
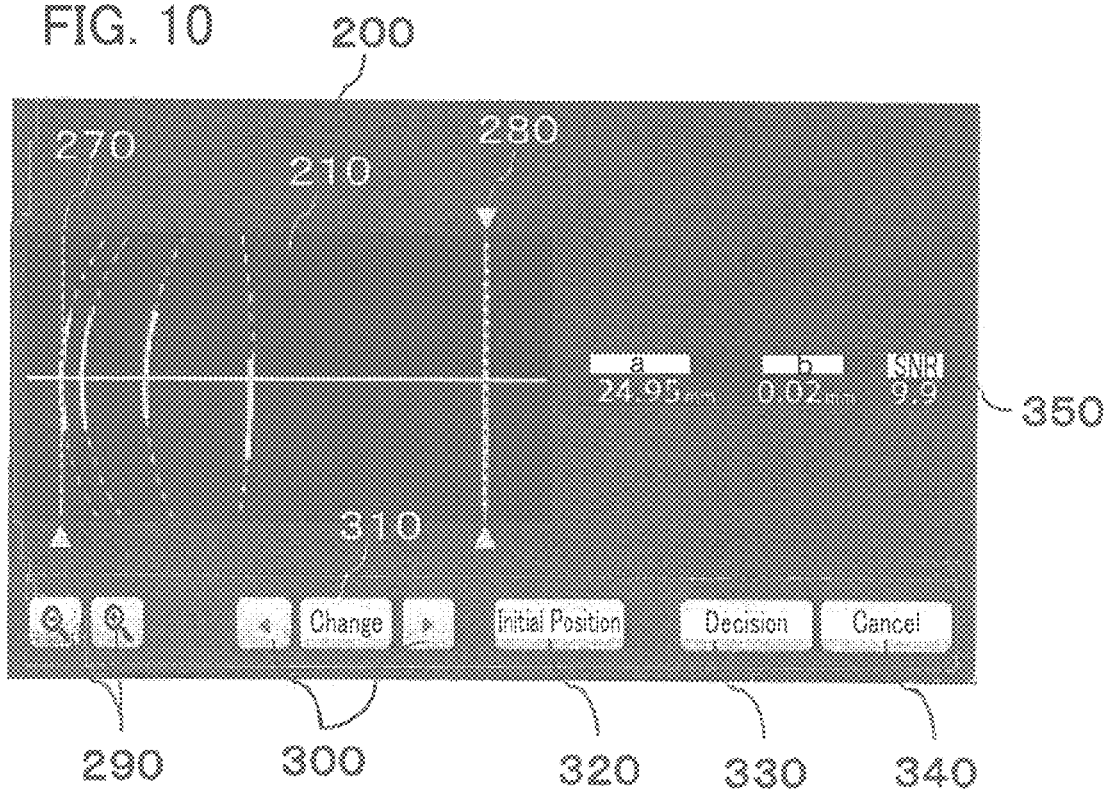
FIG. 10 is an example of a screen display displayed on the monitor (correction mode display).

FIG. 10 is an example of screen display in a correction mode. Where the examiner presses the caliper button 240, the screen displayed on the monitor 62 becomes such as depicted in FIG. 10. Operation buttons 290 to 340 for correction are disposed below the monitor display portion 200. Lines 270 and 280 provided with triangular marks in the image display portion 210 represent a position (270) of the front surface of the cornea and a retina position (280) of the eye 100. Initially, the position (270) of the front surface of the cornea and the retina position (280) calculated with the processor 64 are displayed. The examiner can arrange lines 270 and 280 at adequate positions by using the touch panel function of the monitor 62 or the operation buttons 290, 300, and 310 located in the lower portion of the screen. Once the correction of the position (270) of the front surface of the cornea and the retina position (280) has been completed, a check button 330 is pushed, the corrected positions are stored in the processor 64, computations are repeated, and the corrected values are displayed in the data display portion 350.

The procedure of correcting the position (270) of the front surface of the cornea and the retina position (280) is explained hereinbelow as an example of correction. Initially, the examiner touches the image display portion 210 of the monitor display portion 200 near the line 270 or 280 provided with triangular marks. The monitor in the present example has a touch panel function, and where the monitor display portion 200 is touched, the touching position is computed in the processor 64 and stored.

For example, where the vicinity of the line 270 is touched, the line 270 moves to the touching position. The examiner touches the monitor display portion 200 and the position (270) of the front surface of the cornea is corrected. Where the position is finely determined, the buttons 300 and 310 are used. Where the switching button 310 is pressed, the color of the line 270 or 280 is changed to red. The switching button 310 is pressed such that the line 270 becomes red. Where one of the buttons 300 is pressed in this state, the line 270 moves little by little to the right or to the left. The examiner presses the button 300 such that the line 270 is arranged at the adequate position. The button 290 is pressed when the position is to be determined more strictly. Where a button (enlargement button) to the right of the button 290 is pressed, the periphery of the line 270 is enlarged and displayed, and the examiner adjusts the position of the line 270 by viewing the enlarged displayed image. Such an adjustment may be performed by directly touching the screen or by using the button 300.

The retina position (280) is then corrected. Since the correction sequence is the same as in the case of the position (270) of the front surface of the cornea, the explanation thereof is herein omitted.

An initial position button 320 is for returning the position (270) of the front surface of the cornea and the retina position (280) to the positions before the correction (positions calculated at the time of measurements). A cancel button 340 cancels the corrected position (270) of the front surface of the cornea and retina position (280) and is used when the correction is repeated.

The lines 270 and 280 displayed in the image display portion 210 and the buttons 290 to 340 are merely exemplary, and the lines or operation buttons that can be arranged and displayed are not limited to those shown in FIG. 10. Further, in the explanation hereinabove, the positions to be corrected are the position (270) of the front surface of the cornea and the retina position (280), but the position of the rear surface of the cornea, the position of the front surface of the crystalline lens, and the position of the rear surface of the crystalline lens can be also selected. The number of positions to be corrected has been set to two hereinabove, but this number is not limiting, and the settings may be made such that one or more positions to be corrected can be selected. The position correction operation is not necessarily the touch panel operation, and this operation may be performed using only the buttons 300 and 310. In other words, not all of the operation buttons 290 to 340 are always necessary, and the operation buttons may be arranged as appropriate.

In FIG. 9, the acquired two-dimensional tomographic image is displayed in the monitor display portion 200, but it is also possible to perform the averaging processing of the interference signal information with the processor 64 from the two-dimensional information depicted in FIG. 7, calculate one one-dimensional information (A-scan image) in the depth direction of the eye, and display the calculation result in the monitor display portion 200.

Figure 11:
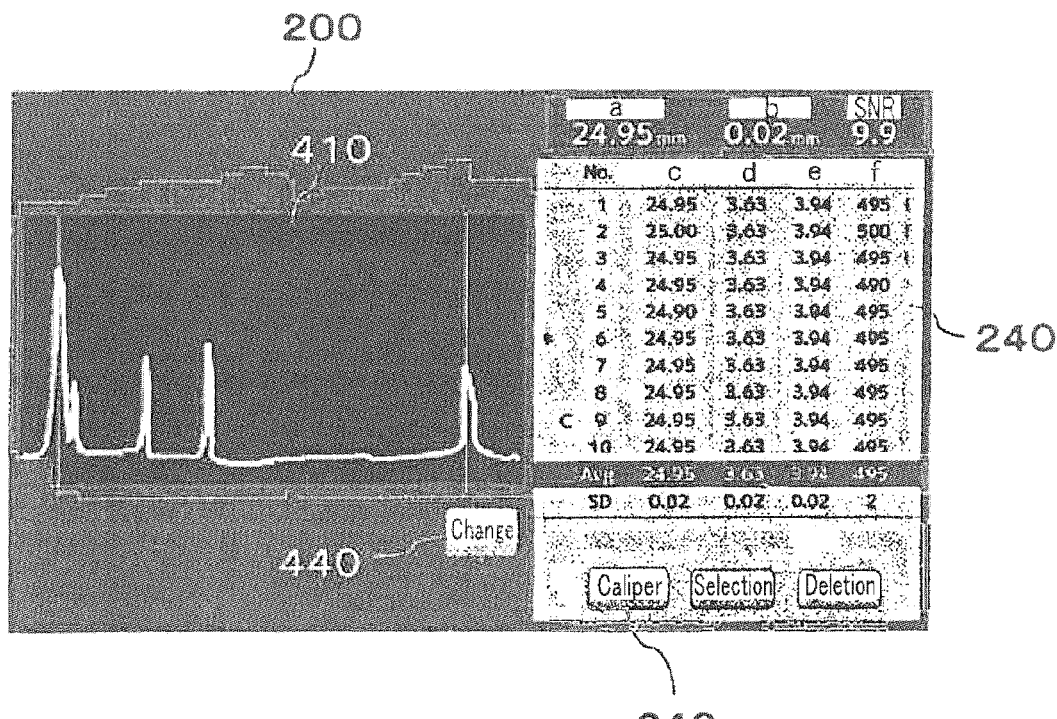
FIG. 11 is an example of a screen display displayed on the monitor (A-scan image display).

FIG. 11 is an example of displaying an A-scan image 410 obtained by averaging processing, instead of using the two-dimensional tomographic image 210 depicted in FIG. 9. As a result, the examiner estimates the measurement value while also checking the A-scan image that has been displayed in the conventional apparatus. The two-dimensional tomographic image and the A-scan image are switched with a switching button 440. Thus, since the examiner can estimate the measurement values while checking both the two-dimensional tomographic image and the A-scan image, the opacity state of the crystalline lens and the retina disease state can be determined easier than with the conventional ophthalmologic apparatus in which only the A-scan image is displayed. As a result, the measurement value can be estimated more efficiently and accurately.

Figure 12:
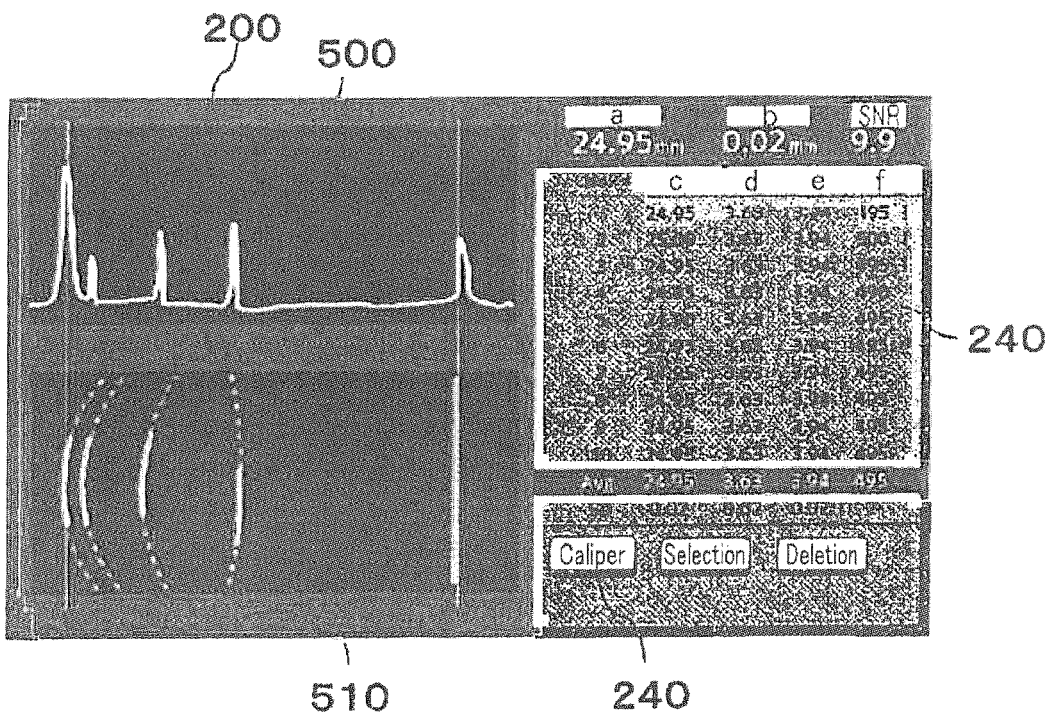
FIG. 12 is an example of a screen display displayed on the monitor (an example in which a two-dimensional tomographic image and an A-scan image are displayed in parallel).

In the example depicted in FIG. 11, the two-dimensional tomographic image and the A-scan image are switched with the switching button, but a two-dimensional tomographic image 510 and an A-scan image 500 may be also displayed in parallel, as depicted in FIG. 12. Where the two images are thus displayed in parallel, the estimation is facilitated by comparison with that illustrated by FIG. 11.

Figure 13:
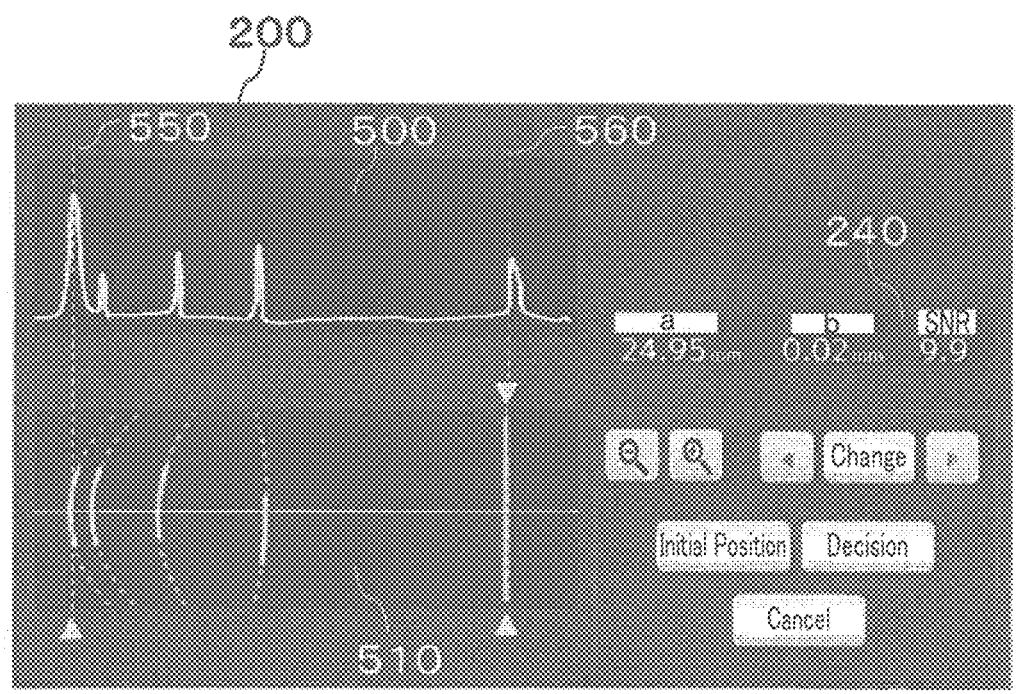
FIG. 13 is an example of a screen display displayed on the monitor (a correction mode in the example in which a two-dimensional tomographic image and an A-scan image are displayed in parallel).

FIG. 13 depicts a screen in the case in which the correction processing illustrated by FIG. 10 is performed in a state in which the two-dimensional tomographic image 510 and the A-scan image 500 are displayed in parallel. The screen depicted in FIG. 13 appears when the caliper button 240 depicted in FIG. 12 is pressed, and the positions such as a position (550) of the front surface of the cornea and a retina position (560) are corrected. Since the correction method is the same as that explained with reference to FIG. 10, the explanation thereof is herein omitted. Where the two images are thus displayed in parallel, the correction is facilitated and the correction accuracy can be increased by comparison with those in the case illustrated by FIG. 10.

Figure 14A:
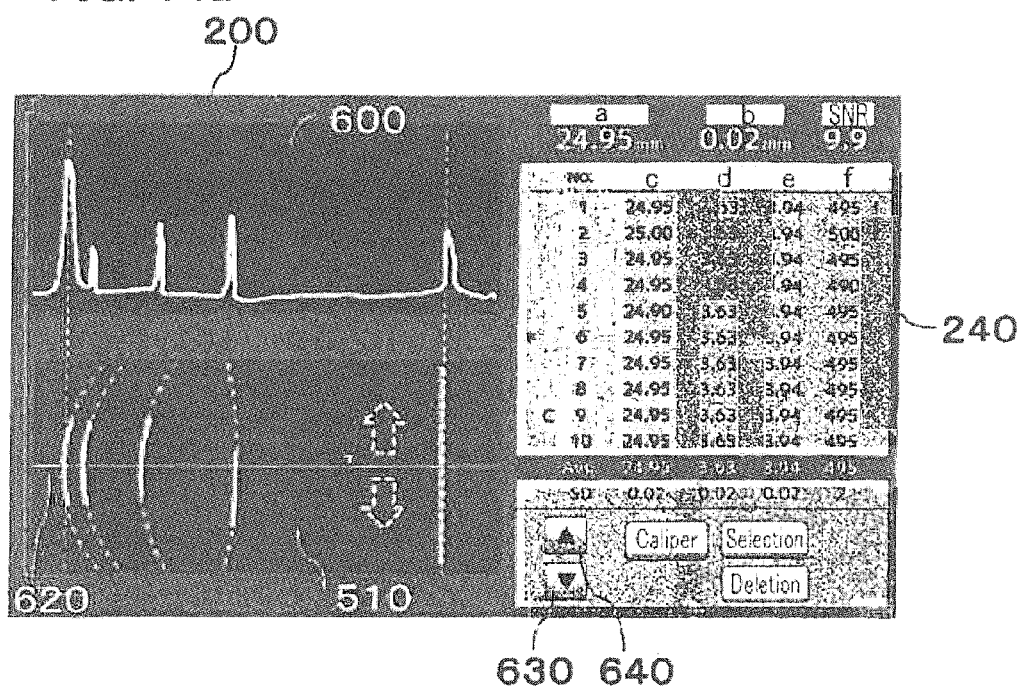
FIG. 14(a) is an example of a screen display displayed on the monitor (an example in which a two-dimensional tomographic image and one selected A-scan image are displayed).
Figure 14B:
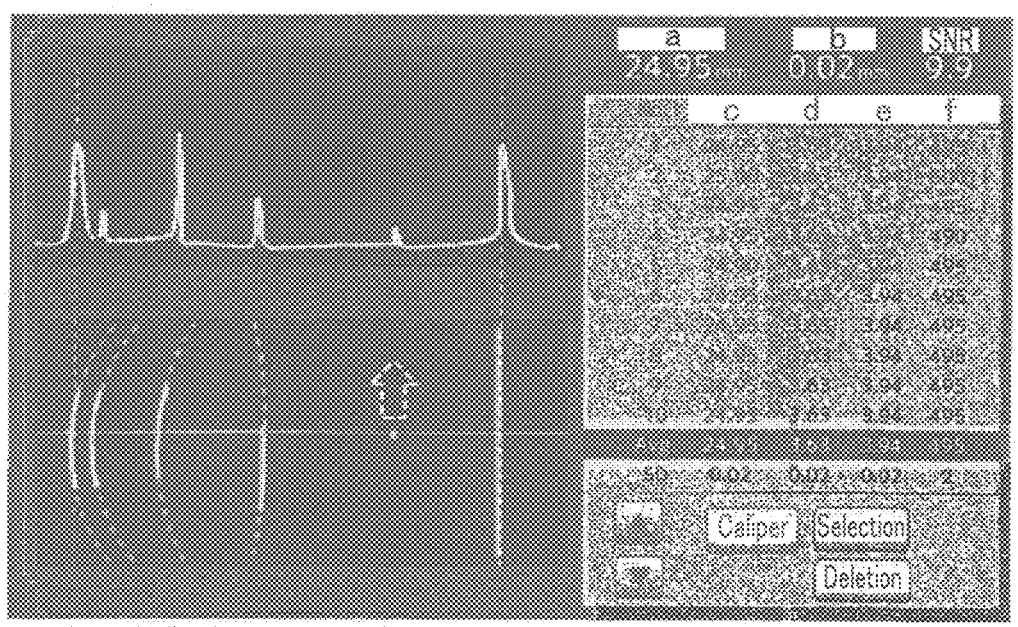
FIG. 14(b) is another example of a screen display displayed on the monitor (an example in which a two-dimensional tomographic image and one selected A-scan image are displayed).

FIGS. 14(*a*) and 14(*b*) illustrate a screen display in an application different from that described hereinabove. An A-scan image 600 is the A-scan image (not the A-scan image subjected to the averaging processing in FIGS. 11 to 13) of interference signals at one optical axis in a line 620 of the two-dimensional tomographic image 510 displayed therebelow. Where the line 620 is moved in the up-down direction, the A-scan image in the depth direction of the eye at the position of the line 620 is displayed. The examiner can obtain detailed information on the interior of the eye by raising and lowering the line 620. Initially, as depicted in FIG. 14(*a*), the line 620 is displayed in the center, in the vertical direction (Y direction) of the two-dimensional tomographic image 510. In the upper A-scan image 600, the A-scan image in the central position in the vertical direction is displayed. Where the examiner touches the vicinity of the line 620 of the two-dimensional tomographic image 510 and moves the line 620 to the position to be checked, the line 620 moves (in this case, upward), as depicted in FIG. 14(*b*), and the A-scan image at the position of the moved line 620 is displayed. The line 620 can be moved by the touch panel operation, as indicated hereinabove, but also can be moved in the up-down direction with the buttons 630 and 640.

In the two-dimensional tomographic image 510 in FIGS. 14(*a*) and 14(*b*), an example is shown in which a small spot is displayed in the middle area of the crystalline lens and the retina. By moving the line 620 to the position where this small spot is located, it is possible to check a waveform state of the portion of the small spot from the data of the A-scan image. Therefore, it is also possible to determine whether or not this spot is a noise. Further, even when a lens opacity is present in the crystalline lens, the opacity state of the crystalline lens can be checked in detail by moving the line 620. By imparting such a function, it is possible to grasp the details of the internal state of the eye as indicated hereinabove.

FIGS. 14(*a*) and 14(*b*) illustrate an example in which one line 620 is displayed, but this number of lines is not limiting, and it is also possible to display a plurality of lines and display a plurality of A-scan images at a plurality of positions in the monitor display portion 200. Since a plurality of A-scan images can be checked at a time, the internal state of the eye can be grasped in greater detail.

Specific examples of the present invention has been described in detail, however, these are mere exemplary indications and thus do not limit the scope of the claims. The art described in the claims include modifications and variations of the specific examples presented above. Technical features described in the description and the drawings may technically be useful alone or in various combinations, and are not limited to the combinations as originally claimed. Further, the art described in the description and the drawings may concurrently achieve a plurality of aims, and technical significance thereof resides in achieving any one of such aims.

What is claimed is:

1. An ophthalmologic apparatus that measures, by light interference, a dimension of an eye to be examined, the ophthalmologic apparatus comprising:
   a light source;
   an incidence unit that causes light from the light source to be incident on a plurality of different positions in the eye to be examined;
   an acquisition unit that acquires a two-dimensional tomographic image of an interior of the eye to be examined on the basis of a plurality of interference signals acquired as a result of the incidence unit causing the incidence of light on the plurality of different positions;
   a first calculation unit that calculates an axial length value of a measuring portion inside the eye to be examined by determining positions of a front surface and a rear surface of the measuring portion on the basis of the plurality of interference signals;
   a display unit that displays the acquired two-dimensional tomographic image; and
   a correction unit that corrects the axial length value of the measuring portion from the two-dimensional tomographic image displayed by the display unit;
   wherein the display unit displays the positions of the front surface and the rear surface determined by the first calculation unit with the acquired two-dimensional tomographic image, and
   the correction unit comprises:
      a first designation unit that designates a new position for at least one of the positions of the front surface and the rear surface with respect to the two-dimensional tomographic image displayed by the display unit; and
      a second calculation unit that recalculates the axial length value on the basis of the new position designated by the first designation unit.

2. The ophthalmologic apparatus as in claim 1, wherein the display unit performs averaging processing of the plurality of interference signals acquired as a result of the incidence unit causing the incidence of light on the plurality of different positions, and further displays a one-dimensional information (A-scan image) in a depth direction of the eye to be examined.

3. The ophthalmologic apparatus as in claim 2, further comprising:
   a second designation unit that designates one or more positions in a direction perpendicular to a depth direction (Z direction) of the eye to be examined with respect to the two-dimensional tomographic image displayed by the display unit, wherein the display unit displays a one-dimensional information (A scan image) in the depth direction of the eye to be examined at one or more positions (optical axes) designated by the second designation unit.

4. The ophthalmologic apparatus as in claim 3, wherein the display unit displays the one-dimensional information and the two-dimensional tomographic image in parallel.

5. The ophthalmologic apparatus as in claim 2, wherein the display unit displays the one-dimensional information and the two-dimensional tomographic image in parallel.

6. The ophthalmologic apparatus as in claim 1, further comprising:
   a second designation unit that designates one or more positions in a direction perpendicular to a depth direction (Z direction) of the eye to be examined with respect to the two-dimensional tomographic image displayed by the display unit, wherein
   the display unit displays a one-dimensional information (A scan image) in the depth direction of the eye to be examined at one or more positions (optical axes) designated by the second designation unit.

7. An ophthalmologic apparatus that measures, by light interference, a dimension of an eye to be examined, the ophthalmologic apparatus comprising:
   a light source;
   an incidence unit configured to cause light from the light source to be incident on a plurality of different positions in the eye to be examined;
   a processor configured to acquire a two-dimensional tomographic image of an interior of the eye to be examined on the basis of a plurality of interference signals acquired as a result of the incidence unit causing the incidence of light on the plurality of different positions, and configured to calculate an axial length value of a measuring portion inside the eye to be examined by determining positions of a front surface and a rear surface of the measuring portion on the basis of the plurality of interference signals; and
   a display unit configured to display the acquired two-dimensional tomographic image; wherein
   the display unit displays the determined positions of the front surface and the rear surface with the acquired two-dimensional tomographic image, and
   the processor is further configured to designate a new position for at least one of the determined positions of the front surface and the rear surface with respect to the two-dimensional tomographic image displayed by the display unit, and configured to calculate the axial length value on the basis of the two-dimensional tomographic image and the designated new position.

8. The ophthalmologic apparatus as in claim 7, wherein
   the display unit is configured to designate one or more positions in a direction perpendicular to a depth direction (Z direction) of the eye to be examined with respect to the displayed two-dimensional tomographic image, and
   the display unit is further configured to display a one-dimensional information (A scan image) in the depth direction of the eye to be examined at one or more positions (optical axes) designated by the display unit.

* * * * *